United States Patent [19]

Wesseldine

[11] Patent Number: 4,577,591
[45] Date of Patent: Mar. 25, 1986

[54] INCONTINENCE AND PROTECTIVE DEVICE FOR ANIMALS

[76] Inventor: Dianne M. Wesseldine, 313 Willard St., Minoa, N.Y. 13116

[21] Appl. No.: 691,204

[22] Filed: Jan. 14, 1985

[51] Int. Cl.⁴ ............................................. A01K 23/00
[52] U.S. Cl. .................... 119/143; 604/398; 128/107
[58] Field of Search .................. 119/95, 143; 128/106, 128/107, 112; 604/397, 398; 54/79

[56] References Cited

U.S. PATENT DOCUMENTS

| | | | |
|---|---|---|---|
| 2,539,606 | 1/1951 | Bailey | 119/143 |
| 2,555,434 | 6/1951 | Anderson | 604/397 X |
| 3,658,064 | 4/1972 | Pociluyko | 604/398 X |
| 3,738,330 | 6/1973 | Alofsin | 119/143 |

FOREIGN PATENT DOCUMENTS

| | | | |
|---|---|---|---|
| 3132671 | 4/1982 | Fed. Rep. of Germany | 119/95 |
| 683622 | 6/1930 | France | 119/143 |
| 943116 | 11/1963 | United Kingdom | 119/143 |
| 981247 | 1/1965 | United Kingdom | 119/143 |

*Primary Examiner*—Robert P. Swiatek
*Attorney, Agent, or Firm*—Bruns and Wall

[57] ABSTRACT

An incontinence and surgical protective device for use by an animal having a flexible pad holder having a pocket formed therein for removably containing a disposable pad. The pad has a semi-rigid frame which provides additional strength to the holder. Elastic straps are used to secure the pad holder to the torso of the animal. Velcro fasteners are sewn into the straps which permits the device to be fitted to animals of various sizes and shapes.

14 Claims, 6 Drawing Figures

INCONTINENCE AND PROTECTIVE DEVICE FOR ANIMALS

BACKGROUND OF THE INVENTION

This invention relates to an incontinence and protective device including an inserted sanitary pad for animals which are domesticated, held in zoos and/or game preserves. The disposable sanitary pad is for absorbing and retaining potentially harmful body fluids that might be discharged by the animal.

Many domestic and/or captive animals, upon reaching old age, lose control over many of their body functions and, if not closely watched, will urinate while indoors or while traveling via automobile, air, train or other modes of transportation. Animal urine is known to contain chemical ingredients that have a harsh effect upon contacting various fabrics and, in particular, dyed fabrics that are used widely in rugs and furniture coverings. As a consequence, soiling these materials with animal urine can produce deep stains that are difficult, if not impossible, to remove using conventional cleaning methods. Similarly, a domestic animal that has experienced recent surgery may have a draining wound which, if left unprotected, can also soil fabrics and other materials coming in contact therewith. Beyond causing stains, this type of animal discharge usually produces lingering unpleasant odors and can create unsanitary conditions in normally occupied quarters.

A leather harness for supporting a waste catching bag or receptacle beneath the torso of an animal is disclosed in U.S. Pat. No. 4,290,386. The harness involves a plurality of straps that are adapted to pass about the animal torso both longitudinally and circumferentially. The straps are buckled tightly in place to suspend a bag beneath the animal's rectum and a pad beneath its inguinal region. The tightly buckled leather straps seriously impede the animal's ability to move about or sit down. The harness is also difficult to fit to the animal's torso and is extremely uncomfortable. The pad cannot be brought beneath the hind legs of the animal and thus severely restricts the use of the device. Furthermore, because of its leather construction, the harness cannot be easily laundered or cleansed.

A similar device for collecting animal waste products is further disclosed in U.S. Pat. No. 3,090,356. Here again a complex system of straps are used to hang a pair of refuse bags beneath the animal's anal and urinary cavities in an effort to catch discharged waste. Because of its bulkiness, the device prevents the animal from either sitting or lying down and is thus a source of potential discomfort to the animal. In the event the animal does attempt to sit or lie down, the contents of the bag will more than likely spill.

Another animal refuse collecting device is described in U.S. Pat. No. 4,095,562 in which a refuse bag is housed in a closely fitted jacket that fits about the rear part of the animal's torso. The jacket includes a zipper fastener and three flap fasteners that are designed to pass between the animal's hind legs and rear flanks. The jacket must be fitted to a specific animal and is thus relatively expensive. Furthermore, because of the tightness of the fit, the jacket can damage the animal fur and, in particular, its underwool. The jacket can also produce overheating of the animal when worn on hot days or indoors.

SUMMARY OF THE INVENTION

It is therefore an object of the invention to improve animal incontinence and surgical protective devices.

A further object of the present invention is to provide an animal incontinence and surgical protective device that can be easily fitted to an animal's torso.

A still further object of the present invention is to provide an animal incontinence and surgical protective device that is simple in construction and which will not discomfort the animal.

Another object of the present invention is to provide an animal incontinence and surgical device that is easily washable.

These and other objects of the present invention are attained by means of an animal incontinence and protective device that includes a pad retainer that is sewn together from a flexible material to form a pocket therein for removably containing a disposable pad. The pad has an absorbent core that is mounted within a semi-flexible frame which, in assembly, adds body to the pad retainer. Elastic straps are employed to draw the retainer securely and comfortably against the inguinal region of the animal and are closed by Velcro fasteners to exert a continuous biasing pressure against the pad.

BRIEF DESCRIPTION OF THE DRAWINGS

These and other objects of the present invention will be described in greater detail in reference to the following description of the invention which is to be read in conjunction with the accompanying drawings, wherein.

DESCRIPTION OF THE INVENTION

Figure 1:
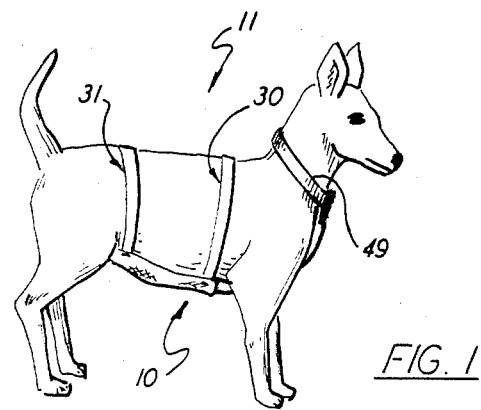
FIG. 1 is a perspective view of a domestic animal which is fitted with an incontinence and/or surgical protective device embodying the teachings of the present invention.
Figure 2:
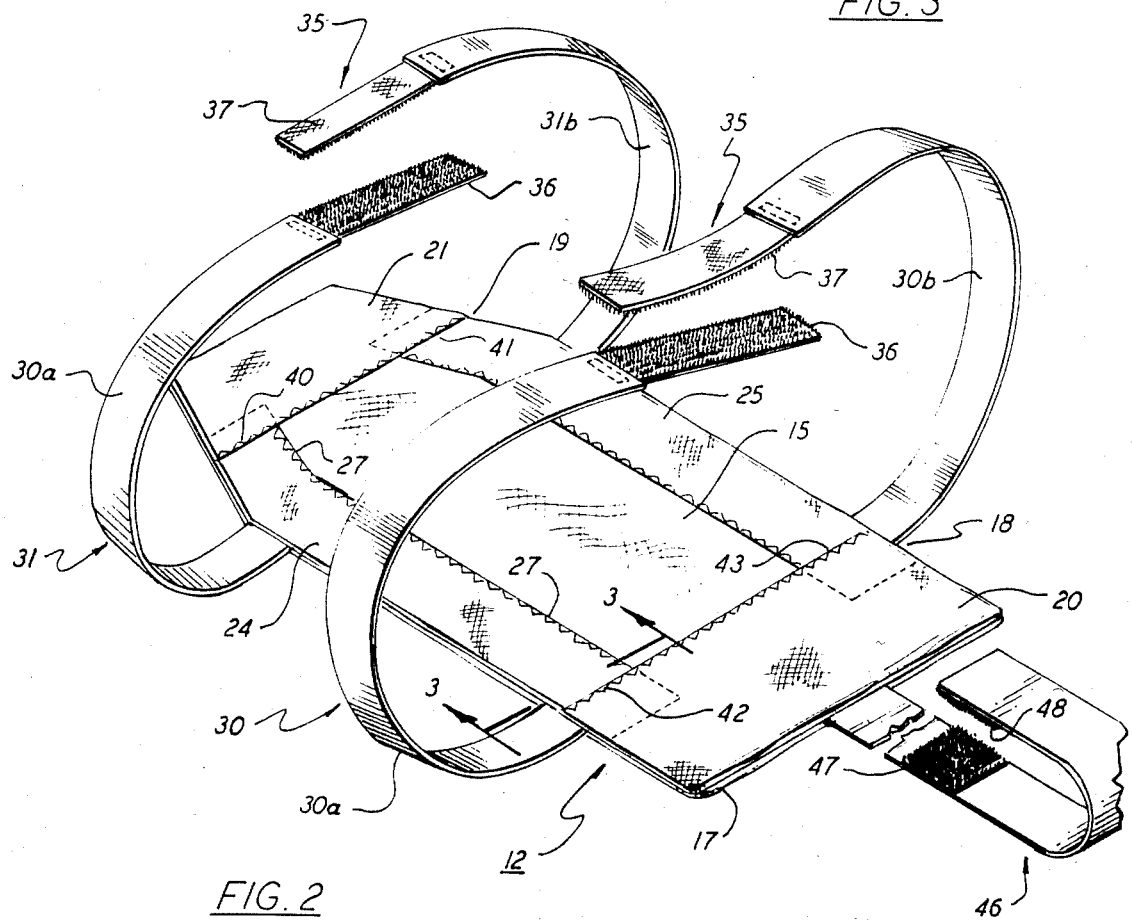
FIG. 2 is an enlarged perspective view of the device shown in FIG. 1.

Referring initially to FIGS. 1–4, there is shown one embodiment of the instant invention that involves an incontinence and/or surgical protective device 10 for covering the inguinal region of a four legged animal, such as a dog 11. The device 10 as illustrated in FIG. 2 is primarily suited for use as an incontinence device for use by a male animal but can be used equally as well as a protective device for either male or female animals that have experienced recent abdominal surgery. The device is specifically designed to provide for both the safety and comfort of the animal while at the same time preventing body fluids from soiling rugs, furniture and the like that the animal might come in contact with. As noted above, most devices of this type are extremely complex and are difficult to fit to the animal's torso. These prior art devices further impede the animal's ability to move about and oftentimes prevents it from sitting or lying down. As will become apparent from the disclosure below, the present device can be quickly and comfortably fitted to the animal's torso, easily secured in place and is readily washable to keep the protected areas clean and thus reduce the risk of infection.

The device includes a pad holder 12 that is made of a flexible cloth material, such as cotton, that can be laundered repeatedly without harm. The holder includes an upwardly facing pocket, generally referenced 15, that is capable of removably containing an absorptive sanitary pad 16 (FIG. 4) which, in practice, is held securely against the underside of the animal. The holder is made up a series of panels that are sewn together to provide a structure having sufficient body strength to maintain its desired shape yet being flexible enough to conform to the animal's torso.

The holder includes a bottom panel 17 having a first rectangular forward section 18 that is integral with a second tapered back section 19 which is arranged to pass between the hind legs of the animal as shown in FIG. 1. Positioned over the bottom panel are a series of packet forming facing panels. The term "facing", as herein used, refers to a strip of contrasting material that is seamed into the bottom panel to form the above noted pocket 15. The facing panels include a front facing panel 20, a back facing panel 21, and a pair of side facing panels which are designated as the right side facing panel 24 and the left side facing panel 25. Each of the facing panels are cut so that they will complement the bottom panel along its peripheral margin as illustrated in FIG. 2.

Each of the facing panels is fully lined with interfacing 26 (FIG. 3) that is sewn into the back of each panel to furnish additional body strength and support. Here again the term "interfacing" is used to identify a strip of lining material that complements the overlying facing panel. The interfacing is joined to the associated facing panel by means of edge stitching as shown at 27 in FIG. 2 which prevents the tips from separating and protects the fabric against fraying. Here again the interfacing is made from a fabric that is washable and which has a shrink coefficient that is about the same as the panel fabric to prevent the assembly from curling after it has been washed.

Figure 3:
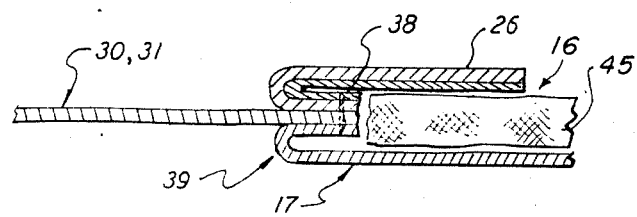
FIG. 3 is a sectional view taken along line 3—3 in FIG. 2.

As best illustrated in FIG. 3, the outer peripheral edges of the bottom panel and the facing panels are turned under and sewn together at 38 to form a seam 39 extending about the entire edge of the pad holder. The seam is closed using any well-known seam stitching technique. In assembly, the two side facing panels 24 and 25 are brought under the front and back facing panels, 20 and 21 respectively, and the overlapping edges of the front and back panels are sewn into the side panels at 40–43. Sewing the panels together in the manner noted thus forms the noted open pocket 15 in the top of the holder which is capable of removably receiving sanitary pad 16 therein.

Figure 4:
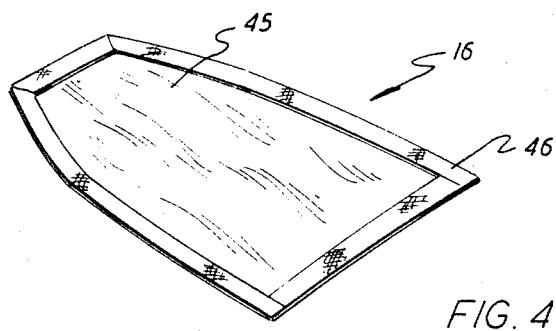
FIG. 4 is a perspective view of a disposable pad that is removably contained within the device shown in FIG. 2.

Pad 16 is a replaceable or throw-away element that is discarded once it has become soiled or has absorbed a sufficient amount of fluid. The pad 16 as shown in FIG. 4 contains a core 45 that includes a downy soft absorbent fill that is non-irritating and non-abrasive to the animal's skin or hair. The core can be filled with an abundant amount of fluffed cellulose for this purpose. The core of the pad is backed with a taffeta textured polyethylene which provides a moisture proof barrier for the structure. The entire peripheral edge of the pad is seated against leakage and an outer frame 46 made of a stiff flexible paperboard (cardboard) is affixed to the edge of the pad. The frame 46 may be further provided with an adhesive coating that will adhere to the facing panels of the holder. Here again, the frame complements the general shape or geometry of the bottom panel 17 and is formed slightly undersized so that it can be passed underneath the facing panel to fit snugly inside the pocket 15. Once inserted into the pocket, the frame of the pad with a wide adhesive strip reinforces the pad holder structure so that it will retain its shape. When the holder is drawn against the underside of the animal's torso, as will be explained in greater detail below, the pad and holder assembly will firmly but comfortably conform to the body contour of the animal to enclose the body region that is being protected regardless of its location.

A pair of straps 30 and 31 are secured to the body of the retainer and are arranged so they can encircle the torso of the animal. As shown in FIG. 1, each strap is made up of two separable bands which are identified as 30a and 30b for the front strap 30 and 31a and 31b for the rear strap 31. Each strap is furnished with a centrally located fastener 35 which permits the straps to be closed about the animal's body. In practice, each fastener is a Velcro closure device having a hook pad 36 sewn into one of the strap bands and loop pad 37 sewn into the other coacting band. The Velcro pads are of sufficient length to permit the straps to be adjusted about the animal's torso whereby the device can be fitted to animals of various sizes and shapes. Preferably, the straps are made of an elastic fabric that is capable of stretching slightly when placed under tension to deliver a continuous holding pressure when tightened in assembly against the holder.

A third front strap 46 formed of an elastic material is similarly sewn into the seam at the front of the pad holder. The strap includes a velcro loop pad 47 and hood pad 48 which can be joined to form a loop at the front on the strap. As illustrated in FIG. 1, the front strap is brought beneath the animal's collar 49 and is loop backed upon itself and fastened using the Velcro fasteners. The front strap is also secured in place to exert a slight biasing force on the strap and thus prevent the pad holder from moving laterally in regard to the animals torso.

As illustrated in FIG. 2 and 3, two ends of the front strap 30 are brought beneath the panels on opposite sides of the pad holder near the point where the front facing panel joins the side panels. The bands are secured to the front of the retainer by sewing the two ends into seam 39. The two ends of the rear strap 31 are similarly sewn into the seam at the rear of the rectangular section where it joins the tapered rear section of the retainer. As can be seen, the rear strap can be brought into abutting contact with the hind legs of the animal (FIG. 1) to position the tapered section of the retainer rearwardly between its legs thus providing extended pad coverage in this region. As noted above, the construction of the pad, as well as the pocket, provides sufficient body strength to the holder so that this part of the holder is supported against the underside of the animal when the straps are tightened about its torso. Sewing the straps into the retainer as herein described permits the elastic straps to be drawn closed by the Velcro fasteners in an extended or stretched condition whereby a continuous biasing pressure is sufficient enough to hold the pad tightly against the protected region but insufficient to cause the animal harm or pain. Once the device has been fitted to the animal, the animal can move freely about without discomfort. The animal is further able to sit and/or lie down without dislodging the pad from the protected area thus preventing the soiling of surfaces contacted by the animal.

Figure 5:
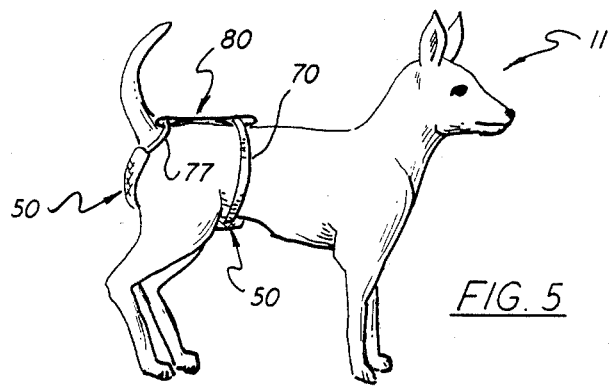
FIG. 5 is also a perspective view of a domestic animal that is fitted with a device illustrating a second embodiment of the present invention.
Figure 6:
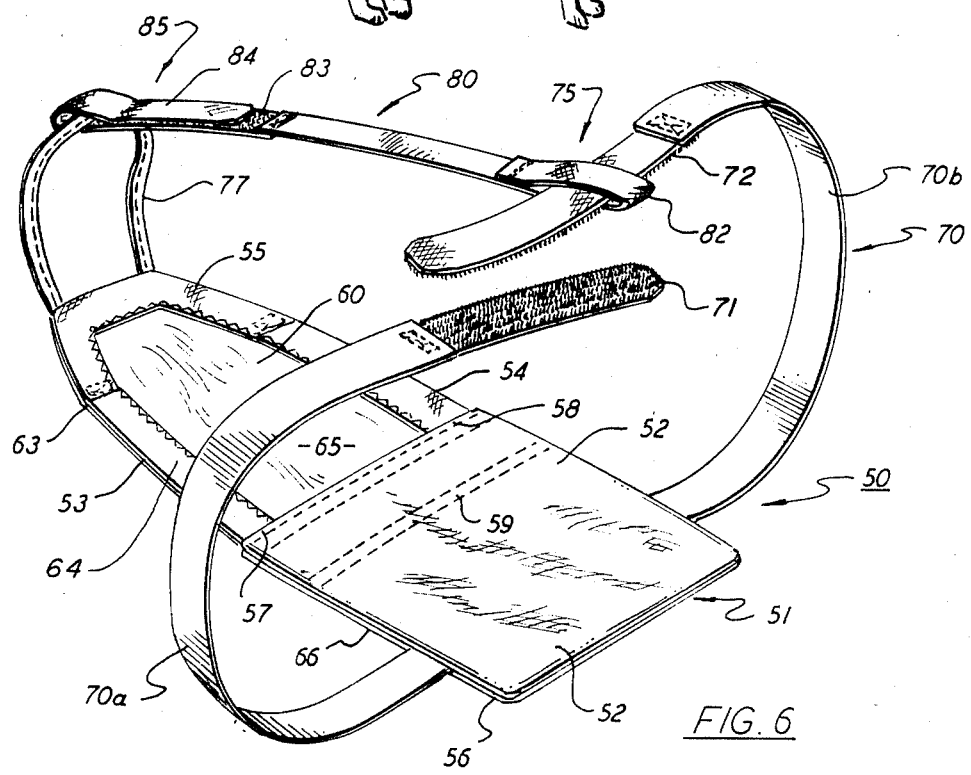
FIG. 6 is an enlarged perspective view of the device illustrated in FIG. 5.

Turning now to FIGS. 5 and 6, there is illustrated a second embodiment of the present invention that is suitable for use by a female animal. A pad holder 50 of the device contains a bottom panel 51, a forward facing panel 52, two side facing panels 53 and 54 and a U-shaped rear facing panel 55. Each of the facing panels is lined with interfacing that is sewn into the underside of the panel as explained above. In this embodiment of the invention, the forward facing panel is arranged to cover almost the entire top surface of the rectangular section 56 of the bottom panel. The side facing panels pass under the forward facing and are again sewed into the facing panels at locations 57 and 58. The forward facing panel is further sewed into the bottom panel along lateral extended lines noted at 59 in FIG. 6.

The side facing panels abut the two ends of the U-shaped rear facing panel 55 to establish a packet opening 60 which is situated at the tapered rear section 63 of the bottom panel. The facing panels are edge stitched at 64 and are seam stitched into the peripheral edge of the bottom panel to form a continuous seam 66 about the pad holder. A replaceable pad 65 having a semi-flexible frame, which is similar in construction to the pad shown in FIG. 4, is removably contained inside the pocket to absorb fluids coming in contact therewith.

A body strap 70 is sewn into the pad holder seam at opposing sides of the rectangular front section. The body strap includes a first elastic band 70a having a Velcro hook pad 71 sewn therein and a second elastic band 70b having a Velcro loop pad 72 sewn therein. The velcro pads form an adjustable fastener, generally referenced 75, for allowing the strap to be closed over the torso of animal II as shown in FIG. 5.

A loop strap 77 is sewn into the peripheral seam 66 at the rear of the pad holder. The loop is adopted to pass over the animal's tail (FIG. 5) to place the pocket opening over the entire inguinal region of the female animal. A safety strap 80 is connected between the body strap 70 and the loop strap 77 to prevent the loop strap from being displaced. A circular eye 82 is sewn into one end of the safety strap that is passed over one of the elastic bands of the body strap. The opposite end of the safety strap contains a Velcro hook pad 83 that is adapted to engage a loop pad 84 to provide an adjustable fastener generally referenced at 85. The fastener is employed to draw the safety strap taut between the loop strap and the body strap and thus prevent the pad holder from shifting its position once it is secured in place.

While this invention has been disclosed with specific reference to the detailed description set forth above, it is not confined to this specific structure and this application is intended to cover any modifications and changes that may come within the scope of the following claims.

I claim:

1. An incontinence and protective device for use on the underside of a four legged animal that includes
    a retainer means formed of a flexible cloth material that includes a bottom panel consisting of a rectangular front section and a tapered rear section for passing between the hind legs of the animal and a series of pocket-forming facing panels overlying the bottom panel that include a pair of side facing panels positioned along the side edges of the bottom panel, a front facing panel positioned over the front section of the bottom panel and a back facing panel positioned over the tapered section of the bottom panel,
    seam means for stitching the facing panels to the bottom panel along its peripheral edge and to each other to form an open topped pocket in said retainer means,
    a sanitary pad removably mounted within the pocket that includes a stiff semi-flexible frame adapted to pass under the facing panels and to retain the shape of the pad when inserted into said retainer means, but conform to the underside of the animal, and an absorptive core attached to the frame that is adapted to fill the pocket opening and thus contact the region on the animal to be protected,
    a pair of two-piece straps that include a first strap having ends sewn into the seam means on opposite sides of the front section of the bottom panel immediately adjacent to the front edge thereof and a second strap having ends sewn into the seam means on opposite sides of the bottom panel immediately adjacent to the rear tapered section, and
    separable fastener means associated with each strap for permitting the straps to pass about the torso of the animal and be secured thereto to apply a gentle holding pressure against the pad mounted in the retainer means.

2. The device of claim 1 wherein said straps are fabricated of an elastic material that is able to stretch against the animal's torso when fastened to apply a continuous pressure upon the pad.

3. The device of claim 2 wherein the fasteners are Velcro fasteners.

4. The device of claim 1 wherein the frame of said sanitary pad is formed of a stiff paper board.

5. The device of claim 1 wherein the retainer means and the straps are fabricated of a washable material whereby they can be cleaned periodically.

6. The device of claim 1 that further includes an elastic front strap also sewn into the seam means at the front of the retainer having a fastening means for attaching the strap to a neck collar worn by the animal to prevent lateral movement of the retainer.

7. The device of claim 1 wherein the core of the pad includes a backing of a taffeta textured moisture proof barrier material.

8. The device of claim 1 wherein the frame is provided with an adhesive coating that will adhere to the facing panels of said retainer means.

9. An incontinence and protective device for use on a four legged animal that includes
    a retainer means formed of a flexible cloth material that includes a bottom panel having a rectangular front section adapted to cover the underside of the animal in front of the hind legs and a tapered rear section adapted to pass upwardly between the hind legs, and a series of pocket forming facing panels overlying the bottom panel that include a pair of side panels that abut a U-shaped back facing panel and a front facing panel covering substantially the entire surface of the front section,
    seam means for stitching the facing panels to the bottom panel along its peripheral edge and to each other to form an open topped pocket in the retainer means,
    a sanitary pad removably mounted in the pocket that includes a semi-flexible frame that is adapted to be received beneath the facing panels and an absorptive core attached to the frame that fills the pocket opening whereby the core is able to contact a protected region, a body strap having a pair of ends that are sewn into the seam means on either side of the front section adjacent the front edge of the bottom panel and a separable fastener for securing the body strap about the torso of the animal in front of the hind legs, a tail strap having a pair of ends that are sewn into the seam means at the rear of the tapered section of the bottom panel to form a loop for passing about the animal's tail whereby the retainer is supported between the hind legs of the animal and brought adjacent said tail, and a safety strap passing about the body strap and the tail strap having an adjustable fastener for permitting the body strap and tail strap to be drawn together and thus secure the retainer means upon the animal.

10. The device of claim 9 wherein the retainer means and the straps are fabricated from a washable material.

11. The device of claim 9 wherein said fasteners are Velcro fasteners.

12. The device of claim 9 wherein the body strap and the safety strap are fabricated of an elastic material.

13. The device of claim 9 wherein the frame of the pad is fabricated of a stiff paper board.

14. The device of claim 9 wherein each of the facing panels contains an interfacing that is sewn into the bottom side of the panel.

* * * * *